United States Patent [19]

Toft et al.

[11] Patent Number: 4,784,979
[45] Date of Patent: Nov. 15, 1988

[54] CATALYST AND CATALYST PRECURSOR CONTAINING VANADIUM AND ANTIMONY

[75] Inventors: Mark A. Toft, Lakewood; James F. Brazdil, Jr., Mayfield Village; Linda C. Glaeser, Cleveland Hts., all of Ohio

[73] Assignee: The Standard Oil Company, Cleveland, Ohio

[21] Appl. No.: 129,263

[22] Filed: Dec. 7, 1987

[51] Int. Cl.$^4$ .................. B01J 23/18; B01J 23/22; B01J 35/08
[52] U.S. Cl. ........................................ 502/8; 502/353
[58] Field of Search ..................... 502/8, 353; 423/593

[56] References Cited

U.S. PATENT DOCUMENTS 3,860,534  1/1975  Harris et al. .................... 502/353
3,873,595  3/1975  Lüssling et al. ................ 502/353 X
3,984,353  10/1976 Sergunkin et al. ............. 502/215 X

*Primary Examiner*—W. J. Shine
*Attorney, Agent, or Firm*—C. S. Lynch; D. J. Untener; L. W. Evans

[57] ABSTRACT

Disclosed is a method of making a catalyst precursor by reacting the ion $VO(O_2)^+$ in aqueous solution with an antimony compound that contains Sb having a valence of 3. In one embodiment, the $VO(O_2)^+$ ion is made by reacting $H_2O_2$ with a vanadium compound.

Also disclosed is making a catalyst by drying and calcining such precursor. When the drying is effected by spray drying a new microspheroidal catalyst is produced. The catalysts useful for ammoxidation of propane are more attrition resistant than catalysts of the same empirical formula made by prior art methods.

18 Claims, No Drawings

CATALYST AND CATALYST PRECURSOR CONTAINING VANADIUM AND ANTIMONY

This invention concerns a method of making catalyst precursors and catalysts containing vanadium and antimony in oxide form, the catalyst precursor so made, and microspheroidal catalyst made from such precursor.

Harris et al. British specifications Nos. 1,336,135 and 1,336,136 disclose making catalysts from $V_2O_5$ and $Sb_2O_5$ slurries that are mixed, dried and calcined. These are used to ammoxidize alkanes such as propane. Harris U.S. Pat. No. 3,860,534 has similar disclosures but the calcined catalyst is washed with water before use to remove soluble vanadium compounds. The dried and calcined material in the Harris method, however, is relatively weak and has low abrasion resistance. More important is the fact that the Harris material in the dried state is a fine talcum powder-like material. Thus, it is not possible to spray dry the Harris slurry to obtain microspheroidal particles large enough for fluidized bed catalysis, generally in the 40-100 micron range.

It is an object of the invention to provide a method of making a catalyst precursor having vanadium and antimony in oxide form, capable of being processed to form a catalyst having good hardness and attrition resistance.

Another object is to provide such a precursor.

A further object is to provide a method of making a hard, attrition-resistant catalyst containing vanadium and antimony in oxide form.

Still another object is to provide a method of making a microspheroidal catalyst containing vanadium and antimony in oxide form, and the microspheroidal catalyst so made.

Other objects, as well as aspects, features and advantages, of the present invention will become apparent from a study of the accompanying disclosure and the claims.

According to one aspect of the invention there is provided a method of making a catalyst precursor having vanadium and antimony in oxide form in the atomic ratio of Sb to V in the range from 0.8 to 4, usually from 1 to 3, by reacting the monoperoxovanadium ion, $VO(O_2)^+$, while in aqueous solution, with an antimony compound which contains Sb having a valence of 3, thereby reducing the average valence of the vanadium to less than 5 and oxidizing antimony to a valence state of 5. At least a portion of the $Sb^{+3}$ is so reduced, not necessarily all.

According to a more specific aspect of the invention, the foregoing is accomplished by reacting $H_2O_2$ in aqueous solution with a vanadium compound and then reacting the antimony compound as above stated. Thus, according to this aspect, there is provided a method of making a catalyst precursor having vanadium and antimony in oxide form in the atomic ratio of Sb to V in the range from 0.8 to 4, usually from 1 to 3, by reacting a vanadium compound with an aqueous hydrogen peroxide solution to form a dispersion containing the monoperoxovanadium ion, $VO(O_2)^+$, in solution, and reacting the latter with an antimony compound which contains Sb having a valence of 3, thereby reducing the average valence of the vanadium to less than 5 and oxidizing antimony to a valence state of 5, wherein the ratio of moles of $H_2O_2$ to atoms of V is at least 1. This ratio can be 1 or any amount over 1, but a ratio of 10 or less is usually sufficient.

The vanadium compound reactant in the latter aspect of the invention can be an inorganic or an organic compound of vanadium, but is usually an inorganic compound. The vanadium in the compound can have any initial valence. A partial list of such compounds includes any oxide of vanadium, such as $V_2O_5$, $V_7O_{13}$, $VO$, $VO_2$, $V_2O_3$, $V_3O_7$, etc.; any vanadium oxyhalide such $VOCl_3$, $VOCl_2$, $(VO_2)Cl$, $VOCl$, $VOBr$, $VOBr_2$, $VOBr_3$; any vanadium halide such as $VF_3$, $VBr_3$, $VCl_2$, $VCl_3$, $VCl_4$, $VF_5$; vanadyl sulfate; meta-vanadic acid; pyro-vanadic acid; in short, any compound of vanadium that will react with an aqueous $H_2O_2$ solution.

The vanadium compound usually used in the reaction with $H_2O_2$ is one of the oxides. Because of availability and cost, $V_2O_5$ is often the compound that is chosen to react with the hydrogen peroxide.

Antimony compound reactants chosen to react with the monoperoxovanadium ion in making the catalyst precursor of the invention can be an organic or an inorganic compound of antimony. A partial list of such compounds includes any of the following types of compounds containing antimony having a valence of 3: any such antimony oxide such as $Sb_2O_3$ and $Sb_2O_4$; $SbOCl$; any such antimony halide such as $SbBr_3$, $SbCl_3$, $SbF_3$ and $SbI_3$.

The antimony compound usually chosen to react with the peroxovanadium ion in either aspect of the invention is one of the antimony oxides containing antimony having a valence of 3. Because of availability and cost $Sb_2O_3$ is ordinarily the chosen oxide. Of course, when the antimony compound is $Sb_2O_4$, the half of the Sb that is 5-valent is not useful to effect reduction of the 5-valent vanadium.

In the aspect of the present process where the $H_2O_2$ reacts with the vanadium compound to produce the peroxovanadium ion, and the latter is thereafter reacted with the antimony compound, the vanadium compound can be contacted with the $H_2O_2$ before it is contacted with the antimony compound, and this has in practice usually been the procedure used. Alternatively, the antimony compound reactant can be present at the initial contact between the vanadium compound and $H_2O_2$, provided that both the V compound reaction with the $H_2O_2$ to form the monoperoxovanadium ion and the oxidation-reduction reaction of the latter with the Sb compound are faster than either the oxidation reaction of the $H_2O_2$ with the Sb compound or the vanadium compound-catalyzed decomposition of the $H_2O_2$. When the V compound is $V_2O_5$ and the Sb compound starting material is $Sb_2O_3$, this procedure can successfully be employed; this is illustrated in Examples 11 and 23. Whether the antimony compound can be present at the initial contact between the V compound and the $H_2O_2$ can be determined by trial and error for other combinations of V and Sb substrates without undue experimentation.

We are aware of U.S. Pat. No. 3,984,353 wherein $Sb_2O_3$ is contacted with $H_2O_2$ and oxidized to $Sb_2O_5$ and the latter is reacted with a compound of certain metals, such as the oxide, and the obtained product is dried and calcined at up to 700° C. The list of second metals includes V. This process, of course, is contrary to the present process. Comparative Example D shows that a catalyst made according to the teachings of this patent is inferior in the ammoxidation of propane, giving only a 6.7 percent per pass conversion of propane and a per pass yield of the sum of acrylonitrile plus HCN plus propylene of only 4.9 percent.

In another aspect of the invention a catalyst precursor is provided which is the product of the process of any one of the foregoing methods.

In still another aspect of the invention there is provided a process for making a catalyst which comprises drying a precursor made by one of the foregoing processes and thereafter calcining the resulting dried product at a maximum temperature in the range 650° to 950° C., usually 700° to 875° C., and most particularly in the range from 750° to 850° C. When the drying is a spray drying step, the product is a microspheroidal catalyst having particle diameters including the range from 10 to 200 microns. The product of the latter process is a new product of the present invention.

The following examples illustrate the invention but are not to be considered in any way limiting.

COMPARATIVE EXAMPLE A

A catalyst was made as taught by Harris U.S. Pat. No. 3,860,534, as follows:

Powdered $V_2O_5$ (27.58 g) and $Sb_2O_3$ (72.56 g) were slurried in 80 cc of water and 80 cc of concentrated nitric acid. The orange slurry was heated on a hotplate until nearly dry, then dried overnight at 130° C. It was then heat treated at 650° C. for 8 hours. It was very soft and powdery.

Half of the catalyst precursor was then mixed with 1 percent of graphite, pelleted, crushed and screened to 20–35 mesh. It was activated by calcining at 810° C. for 1 hour, then cooled to 500° C. and taken from the oven. It was placed in a funnel and washed with warm water running through the catalyst until no color appeared in the filtrate (about 2 hours).

An attrition, or particle size retention, test was carried out on a portion of the activated catalyst. The test procedure is as follows:

A 2 g sample of the catalyst (20/35 mesh) is weighed accurately and placed in a 4 oz. round jar with a screw-on lid, along with 15 BB pellets (4.5 mm., Zn-plated steel). The jar is closed and placed on the rollers of a ball mill. It is then rolled for 1 hour. The contents of the jar are then placed on stacked 20/35 mesh screens to remove any pellets and the fines. The material retained on 35 mesh is then weighed. The particle size retention is reported as percent of the original weight.

The particle size retention was 41%. The same particle size retention test was carried out on an attrition resistant bismuth molybdate type catalyst composition used in commercial fluidized bed propylene ammoxidation operations, and the particle size retention was 78%.

EXAMPLE 1

27.58 g of $V_2O_5$ powder was slurried in 400 cc of water in a 1 liter beaker. While vigorously stirring, 70 g of a 30% $H_2O_2$ solution in water was slowly added and the $V_2O_5$ began to dissolve. This is the step in which the peroxovanadium ion forms. After about 15 minutes some undissolved $V_2O_5$ remained, and another 70 g of the 30% $H_2O_2$ solution was added with continued stirring. The final dispersion was a red solution with some orange flocculent solids.

72.56 g of powdered $Sb_2O_3$ was added to the foregoing dispersion. This dispersion was a catalyst precursor of the claims. The mixture was stirred for about 4 hours with heating in order to reduce the volume by evaporation of water. During this time the dispersion gradually turned to a deep blue-green, then finally to a blackish green. When the mixture could no longer be stirred it was dried in an oven for about 16 hours at 100° C. Thereafter it was calcined for 8 hours at 650° C., cooled and then crushed and seived to 20–35 mesh. The calcined material was very hard.

A portion of this catalyst was activated by calcining for 1 hour at 810° C.

A portion of this catalyst was washed with water in a Soxhlet extractor for several hours until the wash water appeared clear. The washed catalyst was then dried by heating at about 100° C. for about 3 hours. It was still very hard and of a particle size of 20/35 mesh.

The same particle size retention test as in Comparative Example A gave a particle size retention of 92 percent for this catalyst.

EXAMPLE 2

The following procedure was used to make a precursor composition having 1 atom Sb per atom of V. 19.31 g of $V_2O_5$ was slurried in 300 cc water and 96.2 g 30% $H_2O_2$ in two equal parts and stirred 15–20 minutes. 30.79 g $Sb_2O_3$ was added with stirring and the mixture heated to about 100° C.; heating was continued about 5 hours, and water was added to maintain about the original volume. The dispersion so made was a catalyst precursor of the claims.

This precursor was worked up as in Example 1 to produce the final catalyst, which was very hard. It was tested by the attrition or particle size retention test described in Comparative Example A. Its particle size retention was 86 percent.

EXAMPLE 3

27.58 g of powdered $V_2O_5$ were slurried in 500 cc of water and 28 g of 70% $HNO_3$. Two aliquots (70 g each) of 30% $H_2O_2$ were added to this slurry. $Sb_2O_3$ (72.56 g) was added to this slurry and the mixture was heated with stirring for about 2 hours, resulting in a green, homogeneous-appearing slurry. After about 2 more hours heating the slurry becomes dark green and appears to be a solution without solids. This dispersion was a catalyst precursor of the claims. This was refluxed 3 more hours. This was evaporated to near dryness on a hotplate and then dried overnight at 100° C. A black-appearing, very hard solid was obtained. The catalyst was worked up in the same manner as in Example 1, resulting in a washed, very hard catalyst having a particle size of 20/35 mesh.

EXAMPLE 4

This catalyst was prepared by the method of Example 3, except that half the amounts of $V_2O_5$ and $Sb_2O_3$ were used, and 31.25 g of 40% silica sol was added to the green solution before evaporation to dryness. Again, the final catalyst was very hard.

EXAMPLE 5

A catalyst was prepared by the procedure of Example 3, except that the amounts were as follows:
$V_2O_5$: 26.93 g
$Sb_2O_3$: 70.86 g
and 11.90 g of $Fe(NO_3)_3 \cdot 9H_2O$ were added after the green solution formed. This addition resulted in rapid gellation. The gel was partially evaporated on a hotplate, and then dried in an oven for 48 hours at 100° C. Final calcination was at 650° C. for 8 hours followed by 3 hours at 810° C., and the washed catalyst was very hard.

EXAMPLE 6

3.43 g of tin metal was reacted with an aqueous solution of $H_2O_2$ and $HNO_3$ for 1 hour at 80° C. to form a white suspension.

26.38 g of powdered $V_2O_5$ were slurried in 140 g of 30% $H_2O_2$ and 28 g of 70% $HNO_3$. The slurry of the tin compound was then added with stirring. Then 69.41 g of $Sb_2O_3$ was added with stirring and the mixture was stirred for about 2 hours while heating. The resulting green dispersion was a catalyst precursor of the claims. It was evaporated to dryness and was blackish and very hard. It was heated at 650° C. for 8 hours, ground to 20–35 mesh, calcined at 810° C. for 1 hour, washed and dried as in Example 1.

EXAMPLE 7

The following procedure was used to make a precursor composition having 1.3 atoms Sb per atom of V. 11.95 g $V_2O_5$ was slurried in 300 cc water and 82.5 g 30% $H_2O_2$ and stirred 15–20 minutes. 33.79 g $Sb_2O_3$ was added with stirring and the mixture heated to about 100° C.; heating was continued about 5 hours, and water was added to maintain about the original volume. The dispersion so made was a catalyst precursor of the claims.

This precursor was worked up as in Example 6 to produce the final catalyst, which was very hard.

EXAMPLE 8

The following procedure was used to make a precursor composition having 3 atoms Sb per atom of V. 8.45 g $V_2O_5$ was slurried in 300 cc water and 44 g 30% $H_2O_2$ and stirred 15–20 minutes. 41.39 g $Sb_2O_3$ was added with stirring and the mixture heated to about 100° C.; heating was continued about 5 hours, and water was added to maintain about the original volume. The dispersion so made was a catalyst precursor of the claims.

This precursor was worked up in the same manner as the catalyst precursor of Example 2, resulting in the final catalyst, which was very hard.

EXAMPLE 8A

The catalyst of Example 8 was washed and dried as in Example 1. Its particle size retention was 94 percent, measured as in Comparative Example A.

EXAMPLE 9

The following procedure was used to make a precursor composition having 1 atom Sb per atom of V, plus 30% $SiO_2$ support 27.03 g $V_2O_5$ was slurried in 600 cc water and 140 g 30% $H_2O_2$ (added in two equal portions) and stirred 15–20 minutes. 43.11 g $Sb_2O_3$ was added with stirring and the mixture heated to about 100° C.; heating was continued about 4 hours, and water was added to maintain about the original volume. Then 75 g of a 40% $SiO_2$ sol was added with stirring and heated 1 more hour. The dispersion so made was a catalyst precursor of the claims.

This precursor was worked up as in Example 1 to yield the final catalyst, which was very hard.

EXAMPLE 10

13.46 g $V_2O_5$ was slurried in 600 cc water and 70 g 30% $H_2O_2$ (added in two equal portions) and stirred 15–20 minutes. 35.43 g $Sb_2O_3$ was added with stirring and the mixture heated to about 100° C.; heating was continued about 4 hours, and water was added to maintain about the original volume. Then 10.06 g of an 11.7% $TiO_2$ sol was added with stirring and heated 1 more hour. The dispersion so made was a catalyst precursor of the claims.

This precursor was worked up as in Example 1 to yield the final catalyst, which was very hard.

EXAMPLE 11

13.79 g of $V_2O_5$ and 36.28 g $Sb_2O_3$ were slurried with 70 g of 30% $H_2O_2$ in 4 equal aliquots 10–15 minutes apart, while stirring. The mixture is then heated with continued stirring at about 100° C. for 5 hours, water being added periodically as lost by evaporation or boiling, to maintain the volume approximately constant. The resulting dispersion is a precursor of the claims.

The precursor is dried, calcined at 650° C., ground and screened, calcined at 810° C., washed and dried, all as described in Example 1. It was very hard.

COMPARATIVE EXAMPLE B

A catalyst was prepared starting with $Sb_2O_3$ and $V_2O_5$, according to the method taught by U.S. Pat. No. 3,984,353, as follows:

72.56 g of $Sb_2O_3$ were refluxed for 5 hours in 70 g of 30% $H_2O_2$ and 250 cc water. A milky-appearing sol or suspension was formed. 70 g additional 30% $H_2O_2$ was added and the dispersion was poured into a large beaker containing 27.58 g $V_2O_5$ and this was stirred 15 minutes until evolution of gas bubbles stopped. The resulting orange slurry was the evaporated to near dryness and then dried overnight at 100° C. It was then calcined at 650° C. for 8 hours. It was then broken into large particles calcined at 810° C. for 1 hour, cooled, crushed and sieved to 20–35 mesh, then washed with water and dried, as in Example 1.

The catalysts of the present invention are all useful for the ammoxidation of propane to acrylonitrile and associated products. Examples of such ammoxidations are included in the following specific examples.

In the ammoxidation runs of the following examples, the catalyst is in a tubular ⅜ inch I.D. stainless steel fixed bed reactor. The reactor is equipped with a preheat leg and is immersed in a temperature controlled molten salt bath. The gaseous feed components are metered through mass flow controllers into the bottom of the reactor through the preheat leg. Water is introduced through a septum at the top of the preheat leg, using a syringe pump. The feed is fed to the catalyst for a pre-run time before collection of product; the runs of each example last 30–60 minutes during which the product is collected for analysis.

In the examples the conversion, yield and selectivity are defined as follows:

$$\text{conversion} = \frac{\text{moles propane reacted}}{\text{moles propane charged}} \times 100(\%)$$

$$\text{yield} = \frac{\text{moles product produced}}{\text{moles propane charged}} \times 100(\%)$$

$$\text{selectivity} = \frac{\text{moles product produced}}{\text{moles propane reacted}} \times 100(\%)$$

EXAMPLE 12

In this example the pre-run time was 1 hour. The catalyst was the catalyst of Example 1. The reaction temperature was 470° C. and the molar feed ratios were 5 propane/1 NH$_3$/2 O$_2$/1 H$_2$O. The contact time was 2 seconds.

Results for this and the following ammoxidation runs are shown in Table 1. C$_3$= is propylene. AN is acrylonitrile.

Example 13

In this example the pre-run time was 19 hours. The catalyst was the catalyst of Example 1. The reaction temperature was 470° C. and the molar feed ratios were 5 propane/1 NH$_3$/2 O$_2$/1 H$_2$O. The contact time was 2 seconds.

EXAMPLE 14

In this example the pre-run time was 45 hours. The catalyst was the catalyst of Example 3. The reaction temperature was 470° C. and the molar feed ratios were 5 propane/1 NH$_3$/2 O$_2$/1 H$_2$O. The contact time was 1.1 seconds.

COMPARATIVE EXAMPLE C

In this example the pre-run time was 0.8 hours. The catalyst was the catalyst of Example A. The reaction temperature was 470° C. and the molar feed ratios were 5 propane/1 NH$_3$/2 O$_2$/1 H$_2$O. The contact time was 1.8 seconds.

EXAMPLE 15

In this example the pre-run time was 0.8 hours. The catalyst was the catalyst of Example 4. The reaction temperature was 470° C. and the molar feed ratios were 5 propane/1 NH$_3$/2 O$_2$/1 H$_2$O. The contact time was 1.8 seconds.

EXAMPLE 16

In this example the pre-run time was 0.8 hours. The catalyst was the catalyst of Example 5. The reaction temperature was 460° C. and the molar feed ratios were 5 propane/1 NH$_3$/2 O$_2$/1 H$_2$O. The contact time was 1.0 seconds.

EXAMPLE 17

In this example the pre-run time was 0.8 hours. The catalyst was the catalyst of Example 6. The reaction temperature was 460° C. and the molar feed ratios were 5 propane/1 NH$_3$/2 O$_2$/1 H$_2$O. The contact time was 1.0 seconds.

EXAMPLE 18

In this example the pre-run time was 4 hours. The catalyst was the catalyst of Example 7. The reaction temperature was 470° C. and the molar feed ratios were 5 propane/1 NH$_3$/2 O$_2$/1 H$_2$O. The contact time was 2.1 seconds.

EXAMPLE 19

In this example the pre-run time was 0.8 hours. The catalyst was the catalyst of Example 8. The reaction temperature was 470° C. and the molar feed ratios were 5 propane/1 NH$_3$/2 O$_2$/1 H$_2$O. The contact time was 1.2 seconds.

EXAMPLE 20

In this example the pre-run time was 0.8 hours. The catalyst was the catalyst of Example 9. The reaction temperature was 470° C. and the molar feed ratios were 5 propane/1 NH$_3$/2 O$_2$/1 H$_2$O. The contact time was 3.3 seconds.

EXAMPLE 21

In this example the pre-run time was 0.8 hours. The catalyst was the catalyst of Example 9. The reaction temperature was 470° C. and the molar feed ratios were 5 propane/1 NH$_3$/2 O$_2$/1 H$_2$O. The contact time was 2.4 seconds.

EXAMPLE 22

In this example the pre-run time was 0.8 hours. The catalyst was the catalyst of Example 10. The reaction temperature was 460° C. and the molar feed ratios were 5 propane/1 NH$_3$/2 O$_2$/1 H$_2$O. The contact time was 2.2 seconds.

EXAMPLE 23

In this example the pre-run time was 0.8 hours. The catalyst was the catalyst of Example 11. The reaction temperature was 470° C. and the molar feed ratios were 5 propane/1 NH$_3$/2 O$_2$/1 H$_2$O. The contact time was 2.0 seconds.

Comparative Example D

In this example the pre-run time was 0.8 hours. The catalyst was the catalyst of Comparative Example B. The reaction temperature was 470° C. and the molar feed ratios were 5 propane/1 NH$_3$/2 O$_2$/1 H$_2$O. The contact time was 2.2 seconds.

EXAMPLE 24

A microspheroidal catalyst having the empirical formula VSb$_{1.65}$O$_x$ was made as follows:

1378.95 g of powdered V$_2$O$_5$ was added to 30 liters of water at 35° C. contained in a 30 gallon reactor while stirring. About 7000 g of 30% aqueous H$_2$O$_2$ was added over 5 minutes. The temperature rose to 51° C. and then the reactor cooling coils began slowly to lower the temperature. After 30 minutes 3628.20 g of Sb$_2$O$_3$ was slowly added, and the slurry turned pea-green to yellow. The temperature was then raised and held at 95°–100° C. for about 16 hours, then cooled to room temperature. The resulting dispersion was a precursor of the claims.

This dispersion was spray dried. 800 grams of the chamber cut was heated at 650° C. for 8 hours and then calcined at 810° C. for 1 hour. The resulting abrasion-resistant catalyst was spheroidal and was mostly in the size range of 10–200 microns diameter. This was then washed with water as in Example 1.

A portion of this "fluidized bed" catalyst was tested for propane ammoxidation but using a fixed bed. The reaction temperature was 470° C. and the contact time was 2.1 secs. The pre-run time was 1 hour. The feed ratios were 5 propane/1 NH$_3$/2 O$_2$/0.6 H$_2$O. The results are shown in Table 1.

TABLE 1

| Example | Conversion of Propane, % | Yields, % | | | | Selectivities, % | | | |
|---|---|---|---|---|---|---|---|---|---|
| | | AN | HCN | C$_3$= | Sum* | AN | HCN | C$_3$= | Sum* |
| 12 | 11.4 | 7.2 | 1.2 | 0.4 | 8.8 | 62.9 | 10.3 | 3.6 | 76.8 |
| 13 | 12.2 | 7.7 | 1.1 | 0.7 | 9.5 | 63.6 | 9.3 | 5.8 | 78.7 |

TABLE 1-continued

| Example | Conversion of Propane, % | Yields, % | | | | Selectivities, % | | | |
|---|---|---|---|---|---|---|---|---|---|
| | | AN | HCN | $C_3^=$ | Sum* | AN | HCN | $C_3^=$ | Sum* |
| 14 | 13.7 | 7.5 | 1.3 | 1.5 | 10.4 | 55.0 | 9.5 | 11.2 | 75.7 |
| C | 9.7 | 5.6 | 1.2 | 0.4 | 7.2 | 57.8 | 12.4 | 4.0 | 74.2 |
| 15 | 14.1 | 6.5 | 1.5 | 2.4 | 10.4 | 45.8 | 10.9 | 17.0 | 73.7 |
| 16 | 13.3 | 8.1 | 1.3 | 0.5 | 9.9 | 60.7 | 9.6 | 3.5 | 73.9 |
| 17 | 12.9 | 7.9 | 1.3 | 0.6 | 9.7 | 60.9 | 9.7 | 4.3 | 74.9 |
| 18 | 12.6 | 7.4 | 1.5 | 0.6 | 9.4 | 58.4 | 11.6 | 4.5 | 74.5 |
| 19 | 10.2 | 3.5 | 1.3 | 2.6 | 7.5 | 34.5 | 12.4 | 26.0 | 72.9 |
| 20 | 13.7 | 7.7 | 1.6 | 0.6 | 9.9 | 56.6 | 11.6 | 4.3 | 72.5 |
| 21 | 11.3 | 6.7 | 1.4 | 0.4 | 8.5 | 59.5 | 12.3 | 3.2 | 75.0 |
| 22 | 14.0 | 8.3 | 1.4 | 0.6 | 10.3 | 59.0 | 10.0 | 4.5 | 73.5 |
| 23 | 14.1 | 8.0 | 1.4 | 0.9 | 10.3 | 56.9 | 9.8 | 6.4 | 73.1 |
| D | 6.7 | 3.7 | 1.0 | 0.3 | 4.9 | 55.0 | 14.2 | 4.3 | 73.4 |
| 24 | 11.3 | 6.4 | 1.3 | 0.5 | 8.2 | 57.2 | 11.4 | 4.3 | 72.8 |

*of AN + HCN + $C_3^=$

EXAMPLE 25

Another sample of the microspheroidal catalyst of Example 24 was used as the catalyst in the fluidized bed ammoxidation of propane in a 1.5 inch laboratory reactor. The temperature was 470° C. and the WWH was 0.5. The molar feed ratio was 5 propane/1 NH3/2 O2. No water was used. Analysis of the reactor effluent showed that conversion of the propane was 9.1 percent and acrylonitrile selectivity was 54.8 percent.

The Harris method of making a catalyst and the present method of making a catalyst both produce catalysts active for the ammoxidation of propane. However, the Harris catalyst has less attrition resistance by far. From the Harris precursor slurry, one cannot obtain a dried catalyst having spheroidal particles of a size large enough for commercial fluidized bed catalytic reaction processes. The foregoing examples illustrate these points.

In the results shown in Table 1, the acrylonitrile and HCN products are valuable primary products, although it is usually preferred to have the AN yield high in relation to HCN. The propylene is also a valuable product since acrylonitrile can be made therefrom by ammoxidation.

As will be evident to those skilled in the art, various modifications of this invention can be made or followed in the light of the foregoing disclosure and discussion without departing from the spirit and scope of the disclosure or from the scope of the claims.

We claim:

1. A method of making a catalyst precursor having vanadium and antimony in oxide form in the atomic ratio of Sb to V in the range from 0.8 to 4, by reacting the monoperoxovanadium ion, $VO(O_2)^+$, while in aqueous solution with an antimony compound which contains Sb having a valence of 3, thereby reducing the average valence of the vanadium to less than 5 and oxidizing antimony to a valence state of 5.

2. A method of claim 1 wherein said ratio is in the range from 1 to 3.

3. A catalyst precursor which is the product of the process of claim 1.

4. A method according to claim 1 with the additional steps of drying said precursor and thereafter calcining the resulting dried product at a maximum temperature in the range 650° to 950° C., thereby producing a catalyst.

5. A method of claim 4 wherein said temperature is in the range 700° to 875° C.

6. A method of claim 4 wherein said temperature is in the range 750° to 850° C.

7. A method of claim 1 wherein said vanadium compound is a vanadium oxide.

8. A method of claim 1 wherein said antimony compound is an antimony oxide.

9. A method according to claim 4 wherein the drying step is a spray drying step and the catalyst produced is microspheroidal and has spheroids with particle diameters in the range from 10 to 200 microns.

10. A catalyst which is the product of the process of claim 9.

11. A method of making a catalyst precursor having vanadium and antimony in oxide form in the atomic ratio of Sb to V in the range from 0.8 to 4, by reacting a vanadium compound with an aqueous hydrogen peroxide solution to form a dispersion containing the monoperoxovanadium ion, $VO(O_2)^+$, in solution, and reacting the latter with an antimony compound which contains Sb having a valence of 3, thereby reducing the average valence of the vanadium to less than 5 and oxidizing antimony to a valence state of 5, wherein the ratio of moles of $H_2O_2$ to atoms of V is at least 1.

12. A method of claim 11 wherein said ratio is in the range from 1 to 3.

13. A method according to claim 12 with the additional steps of drying said precursor and thereafter calcining the resulting dried product at a maximum temperature in the range 650° to 950° C., thereby producing a catalyst.

14. A method of claim 13 wherein said temperature is in the range 700° to 875° C.

15. A method of claim 13 wherein said temperature is in the range 750° to 850° C.

16. A method of claim 12 wherein said vanadium compound is a vanadium oxide.

17. A method of claim 12 wherein said antimony compound is an antimony oxide.

18. A method according to claim 13 wherein the drying is a spray drying step and the catalyst produced is microspheroidal and has spheroids with particle diameters in the range from 10 to 200 microns.

* * * * *

UNITED STATES PATENT AND TRADEMARK OFFICE
CERTIFICATE OF CORRECTION

PATENT NO. : 4,784,979
DATED : November 15, 1988
INVENTOR(S) : Mark A. Toft, et al It is certified that error appears in the above-identified patent and that said Letters Patent is hereby corrected as shown below:

Column 1, line 49, "reduced" should read --oxidized--.

Signed and Sealed this

Ninth Day of May, 1989

Attest:

DONALD J. QUIGG

Attesting Officer

Commissioner of Patents and Trademarks